United States Patent
Yoshida et al.

(10) Patent No.: US 11,208,109 B2
(45) Date of Patent: Dec. 28, 2021

(54) DRIVER CONDITION ESTIMATING DEVICE, DRIVER CONDITION ESTIMATING METHOD AND COMPUTER PROGRAM THEREFOR

(71) Applicant: MAZDA MOTOR CORPORATION, Hiroshima (JP)

(72) Inventors: Makoto Yoshida, Aki-gun (JP); Taro Iwamoto, Aki-gun (JP); Ken Ikuhisa, Aki-gun (JP); Yohei Iwashita, Aki-gun (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 0 days.

(21) Appl. No.: 17/103,990

(22) Filed: Nov. 25, 2020

(65) Prior Publication Data
US 2021/0197833 A1 Jul. 1, 2021

(30) Foreign Application Priority Data

Dec. 27, 2019 (JP) .............................. JP2019-238171

(51) Int. Cl.
*G08B 23/00* (2006.01)
*B60W 40/08* (2012.01)
(Continued)

(52) U.S. Cl.
CPC ............ *B60W 40/08* (2013.01); *B60W 50/14* (2013.01); *G06K 9/00335* (2013.01);
(Continued)

(58) Field of Classification Search
CPC .. B60W 40/08; B60W 50/14; B60W 2540/21; B60W 2540/221; B60W 2050/146; G06K 9/00335; G06K 9/00845
(Continued)

(56) References Cited

U.S. PATENT DOCUMENTS 6,927,694 B1 * 8/2005 Smith .................. B60K 28/066
340/573.1
2008/0288143 A1 * 11/2008 Smith ................ G06K 9/00335
701/49
(Continued)

FOREIGN PATENT DOCUMENTS

JP       6361312 B2    7/2018
JP       6379720 B2    8/2018

OTHER PUBLICATIONS

Nakamura et al., "Multiscale Analysis of Intensive Longitudinal Biomedical Signals and Its Clinical Applications", Proceedings of the IEEE, vol. 104, No. 2, Feb. 2016, pp. 242-261.
(Continued)

*Primary Examiner* — Naomi J Small
(74) *Attorney, Agent, or Firm* — Xsensus LLP

(57) ABSTRACT

A driver condition estimating device includes circuitry configured to measure movement of the head of a driver from output of a driver camera and detect a sign of abnormality of the driver from the movement of the head. On condition that lateral acceleration acting on the head of the driver is a predetermined value or less, the circuitry is configured to calculate a periodic feature amount from time series data showing the movement of the head of the driver, calculate a time series variation pattern from the obtained periodic feature amount, and compare of the obtained time series variation pattern with a predetermined threshold.

18 Claims, 12 Drawing Sheets

(51) Int. Cl.
*B60W 50/14* (2020.01)
*G06K 9/00* (2006.01)

(52) U.S. Cl.
CPC ... *G06K 9/00845* (2013.01); *B60W 2050/146* (2013.01); *B60W 2540/21* (2020.02); *B60W 2540/221* (2020.02)

(58) Field of Classification Search
USPC ...................................................... 340/573.1
See application file for complete search history.

(56) References Cited

U.S. PATENT DOCUMENTS

| | | | | |
|---|---|---|---|---|
| 2016/0052391 | A1* | 2/2016 | Walsh | B60K 28/066 340/575 |
| 2016/0128619 | A1* | 5/2016 | Geller | A61B 5/11 600/595 |
| 2019/0005341 | A1* | 1/2019 | Korthauer | G06K 9/00335 |
| 2019/0362133 | A1* | 11/2019 | Margolin | G06K 9/00302 |
| 2021/0241011 | A1* | 8/2021 | Cronje | B60Q 9/00 |

OTHER PUBLICATIONS

Mizuta et al., "Fractal time series analysis of postural stability", Equilibrium Res., vol. 75, No. 3, 2016, pp. 154-161.

\* cited by examiner

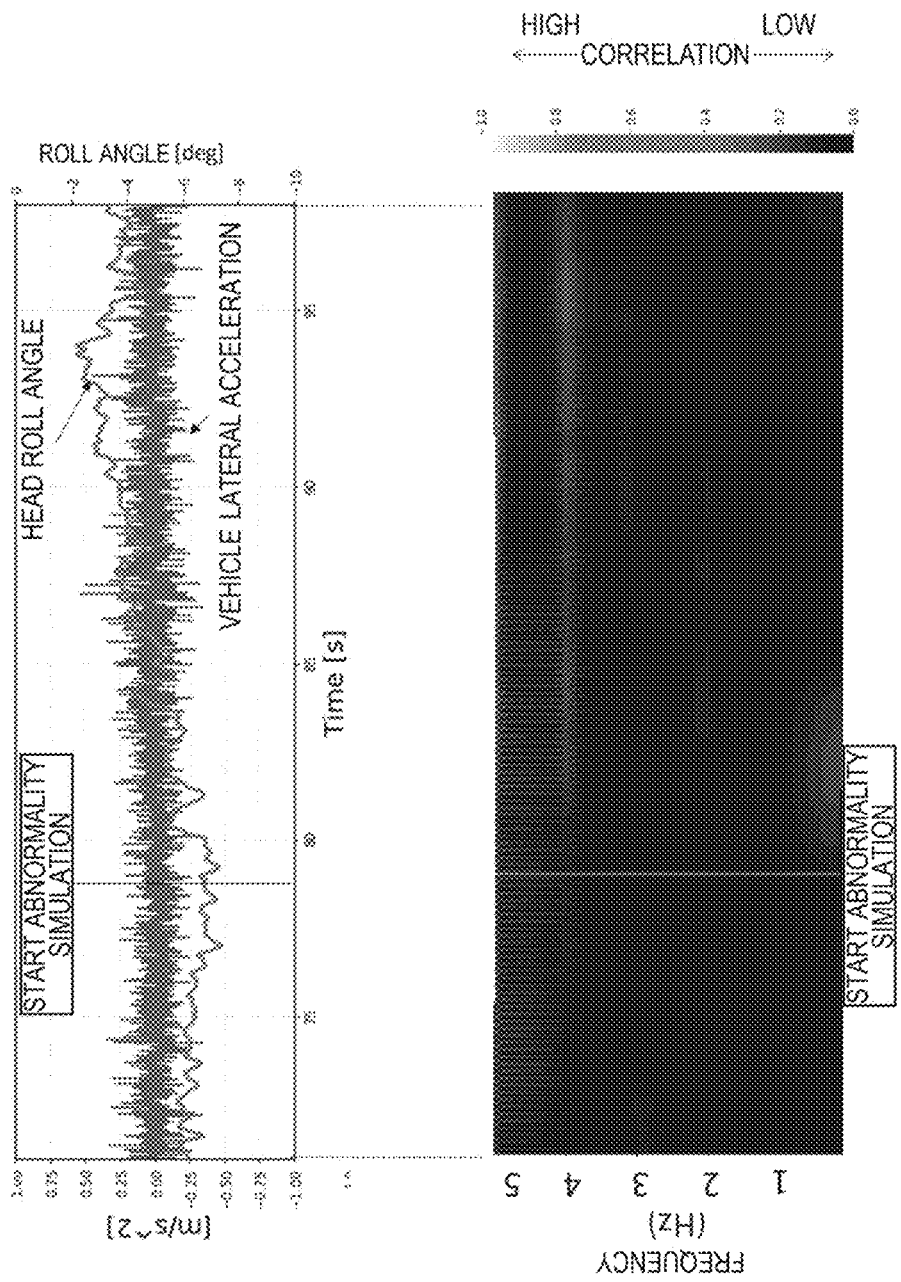

DRIVER CONDITION ESTIMATING DEVICE, DRIVER CONDITION ESTIMATING METHOD AND COMPUTER PROGRAM THEREFOR

CROSS REFERENCE TO RELATED APPLICATION

The present application is based on and claims priority of Japanese Patent Application No. 2019-238171 filed on Dec. 27, 2019, the entire contents of which are incorporated herein by reference.

TECHNICAL FIELD

The technique disclosed herein belongs to a field of technology for estimating condition of a driver who is driving a vehicle.

BACKGROUND ART

Recently, development of automated driving systems is promoted. The applicant of this application has a view that automated driving systems are roughly classified into the following two types.

The first type is a system that an automobile autonomously carries a passenger to a destination without needing operation of a driver, which is so-called "full driving automation" of an automobile. The second type is an automated driving system based on a premise that a person drives, for example, in order to enjoy driving an automobile, while assuming the driver is normally responsible for driving.

The second automated driving system is supposed to make an automobile automatically substitute for a driver and perform automated driving, e.g., in the event that a driver falls ill, falls asleep, and the like, and can no longer drive normally. For this purpose, early detection with high accuracy of occurrence of abnormality in a driver is very important from the point of view of improving a life-saving rate of a driver and securing safety of the driver and the surroundings.

Patent document 1 discloses a technique for detecting loss of the ability to drive of a driver from abnormal direction of the face of the driver as well as non-driving operation or abnormal driving operation. Patent Document 2 discloses a technique for determining occurrence of abnormality in a driver when the head of the driver is moved greatly or slightly by an applied external force.

PRIOR ART DOCUMENTS

Patent Documents

[Patent document 1] JP-B-6379720
[Patent document 2] JP-B-6361312

Non-Patent Documents

[Non-Patent document 1] T. Nakamura, et al., *Multiscale Analysis of Intensive Longitudinal Biomedical Signals and its Clinical Applications*, Proceedings of the IEEE, Institute of Electrical and Electronics Engineers, 2016, vol. 104, pp. 242-261

[Non-Patent document 2] Mizuta et al., *Fractal time series analysis of postural stability*, Equilibrium Research, Japan Society for Equilibrium Research, 2016, Vol. 75(3), pp. 154-161

SUMMARY OF THE DISCLOSURE

As disclosed in Patent documents 1 and 2, techniques for determining loss of the ability to drive of a driver or determining abnormality in a driver on the basis of movement of the head of the driver, are already known. These techniques detect a condition in which the driver loses the ability to drive after the driver falls ill. In order to more safely conduct an action, such as emergency stop, at the time when abnormality occurs in a driver, it is preferable to detect the sign before the driver loses the ability to drive. Early detection of the sign of losing the ability to drive reduces a free running time of a vehicle due to occurrence of an abnormality and makes it possible to more safely conduct an action, such as emergency stop.

One or more embodiments disclosed herein enables early detection of a sign of losing the ability to drive of a driver who is driving a vehicle.

To solve the above problem, the technique disclosed herein includes a driver condition estimating device that is configured to estimate condition of a driver who is driving a vehicle. The driver condition estimating device includes a head movement measuring unit and a detector. The head movement measuring unit is configured to measure movement of the head of the driver from output of a camera that photographs the driver. The detector is configured to detect a sign of abnormality of the driver from the movement of the head measured by the head movement measuring unit. The detector is configured to, in a case in which lateral acceleration acting on the head of the driver exceeds a predetermined value, perform no detection of the sign of abnormality. The detector is further configured to, in a case in which lateral acceleration acting on the head of the driver is the predetermined value or less, calculate a periodic feature amount from time series data showing the movement of the head of the driver, calculate a time series variation pattern from the calculated periodic feature amount, and compare the calculated time series variation pattern with a predetermined threshold to determine existence of the sign of abnormality of the driver.

This technique focuses on a homeostatic maintaining function of a human body and detects a sign of abnormality from movement of the head of a driver. Homeostasis is a function to maintain conditions from disturbances. As for movement of the head, homeostasis makes a driver to maintain the posture of the head during driving. The head of a driver irregularly moves due to the maintaining function of homeostasis in a normal condition but moves slightly and stably in an illness occurring condition. Moreover, the head moves periodically in a condition, called a "critical slowing down" condition, when the condition is changed from the normal condition to the illness occurring condition. In view of this, the inventors of this application came to a thought that a periodic feature amount of movement of the head can be used to detect a sign of abnormality of a driver. Moreover, results of further experiments and investigations showed that the periodicity of movement of the head frequently appears even in the normal condition. However, by classifying time series variation patterns of periodic feature amounts into patterns is effective for distinguishing the normal condition from an abnormality sign appearing condition. In addition, results of further investigation revealed that the periodicity of movement of the head tends to appear in a case in which lateral acceleration greatly acts on the head of a driver, such as traveling around a corner.

Thus, this technique detects a sign of abnormality of a driver from movement of the head of the driver. The head movement measuring unit measures movement of the head of a driver from output of the camera that photographs the driver. The detector for detecting a sign of abnormality of a driver does not detect a sign of abnormality in the case in which lateral acceleration acting on the head of the driver exceeds a predetermined value, but determines existence of the sign of abnormality of the driver in the case in which lateral acceleration acting on the head of the driver is the predetermined value or less, by the following processes: calculation of a periodic feature amount from time series data showing the movement of the head of the driver, calculation of a time series variation pattern from the calculated periodic feature amount, and comparison of the obtained time series variation pattern with a predetermined threshold. As a result, the sign of abnormality of the driver can be detected earlier with high accuracy. In addition, it is possible to measure movement of the head of the driver from a photographic image of the camera placed in the vehicle interior. Therefore, this technique enables early detection of a sign of illness that can cause loss of the ability to drive, by using an existing onboard sensor.

The detector may be configured to determine whether lateral acceleration acting on the head of the driver exceeds the predetermined value, from output of a sensor for measuring a movement state of the vehicle.

Thus, the detector easily recognizes the scene where the sign of abnormality is difficult to detect.

The detector may be configured to dimensionally reduce time series data of the calculated periodic feature amount by using a nonlinear dimensionality reduction method to obtain two-dimensional data as the time series variation pattern, and the detector may be configured to determine existence of the sign of abnormality of the driver from the obtained two-dimensional data by using a determination line in a two-dimensional map as the predetermined threshold.

This enables easy determination of existence of the sign of abnormality of the driver from the time series data of the periodic feature amount of the movement of the head.

The technique disclosed herein also includes a driver condition estimating method for estimating condition of a driver who is driving a vehicle. The driver condition estimating method includes, in a case in which lateral acceleration acting on the head of the driver exceeds a predetermined value, performing no detection of a sign of abnormality. The driver condition estimating method also includes, in a case in which lateral acceleration acting on the head of the driver is the predetermined value or less, calculating a periodic feature amount from time series data showing movement of the head of the driver, calculating a time series variation pattern from the calculated periodic feature amount, and comparing the calculated time series variation pattern with a predetermined threshold to determine existence of the sign of abnormality of the driver.

This technique does not detect the sign of abnormality in the case in which lateral acceleration acting on the head of the driver exceeds a predetermined value, but determines existence of the sign of abnormality of the driver in the case in which lateral acceleration acting on the head of the driver is the predetermined value or less, by these processes: calculation of a periodic feature amount from time series data showing movement of the head of the driver, calculation of a time series variation pattern from the calculated periodic feature amount, and comparison of the obtained time series variation pattern with a predetermined threshold. As a result, the sign of abnormality of the driver can be detected earlier with high accuracy.

As described above, the technique disclosed herein enables early detection of a sign of losing the ability to drive of a driver who is driving a vehicle.

BRIEF DESCRIPTION OF THE DRAWINGS

In FIG. 2, (a) shows a normal condition, (b) shows a critical slowing down condition, and (c) is an abnormality occurring condition.

FIG. 7A is time series data obtained in the normal condition during straight traveling, FIG. 7B is time series data obtained in an abnormality simulating condition, and FIG. 7C is time series data obtained in the normal condition during traveling a corner.

FIGS. 8A and 8B are data of traveling experiments. FIG. 8A is data obtained in entering a corner from a straight section, and FIG. 8B is data obtained while the condition is changed from the normal condition to the abnormality simulating condition.

DETAILED DESCRIPTION

Hereinafter, an exemplary embodiment will be detailed with reference to the drawings.

Figure 1:
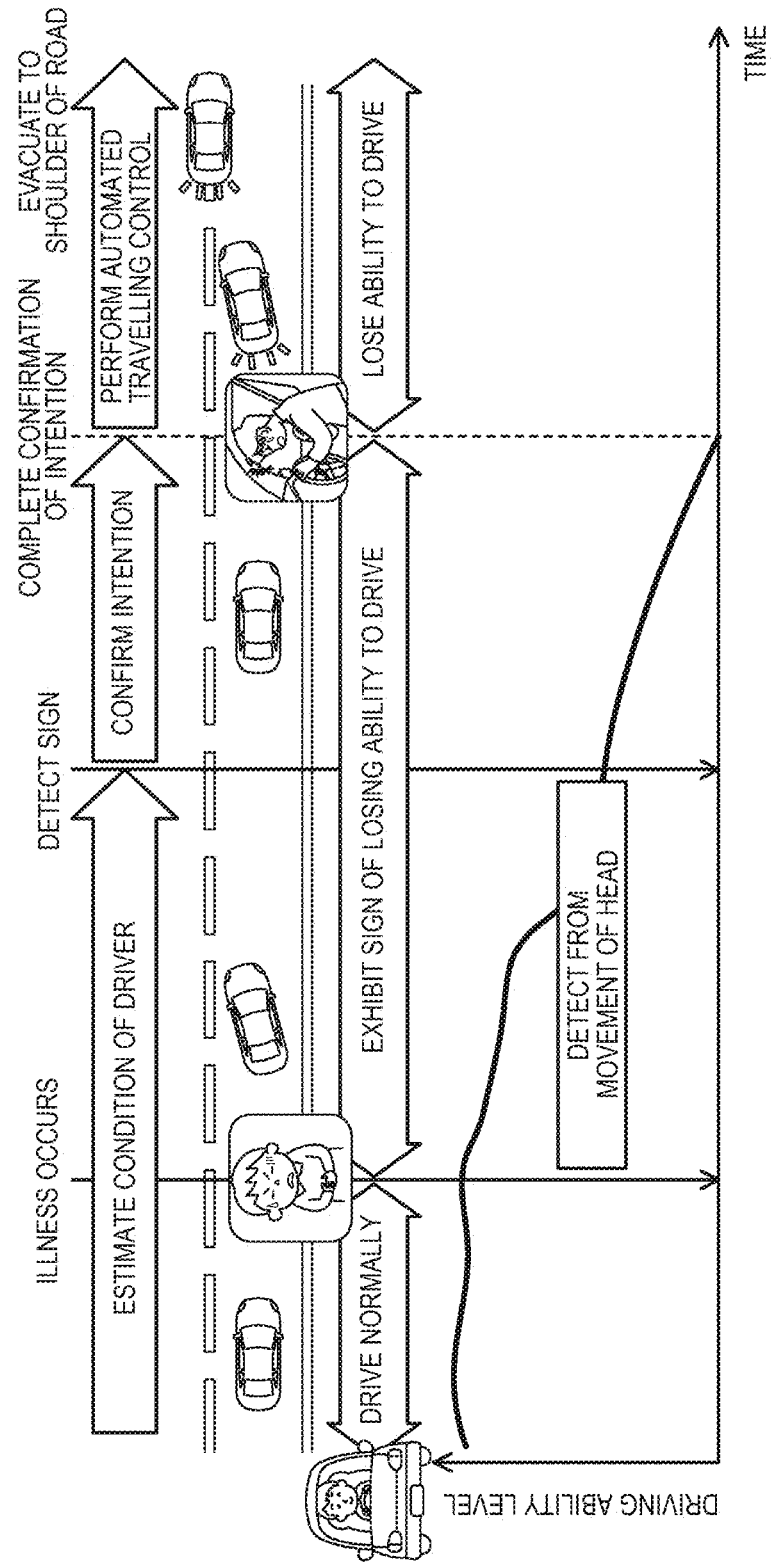
FIG. 1 is a conceptual diagram showing an overview of a technique according to this disclosure.

FIG. 1 is a conceptual diagram showing an overview of a technique according to this disclosure. Patterns of condition change that causes a driver to lose the ability to drive are summarized into three cases. A case "A" is a pattern in which one of functions of perception, judgment, and movement deteriorates first, a case "B" is a pattern in which multiple functions gradually deteriorate, and a case "C" is a pattern in which consciousness is suddenly lost. Among them, in the cases "A" and "B", the level of the ability to drive of a driver is gradually lowered to cause a condition in which the ability to drive is lost, after illness occurs, as shown in FIG. 1. Thus, detecting the condition in which the ability to drive is deteriorated makes it possible to detect a sign of losing the ability to drive of the driver. In the condition in which the sign of losing the ability to drive is detected, an emergence response can be subsequently conducted, for example, such that an intention of the driver is confirmed and the vehicle is evacuated to a shoulder of a road by automatic traveling control.

The technique according to this disclosure focuses on a homeostatic maintaining function of a human body and detects a sign of losing the ability to drive from movement of the head of a driver.

Figure 2:
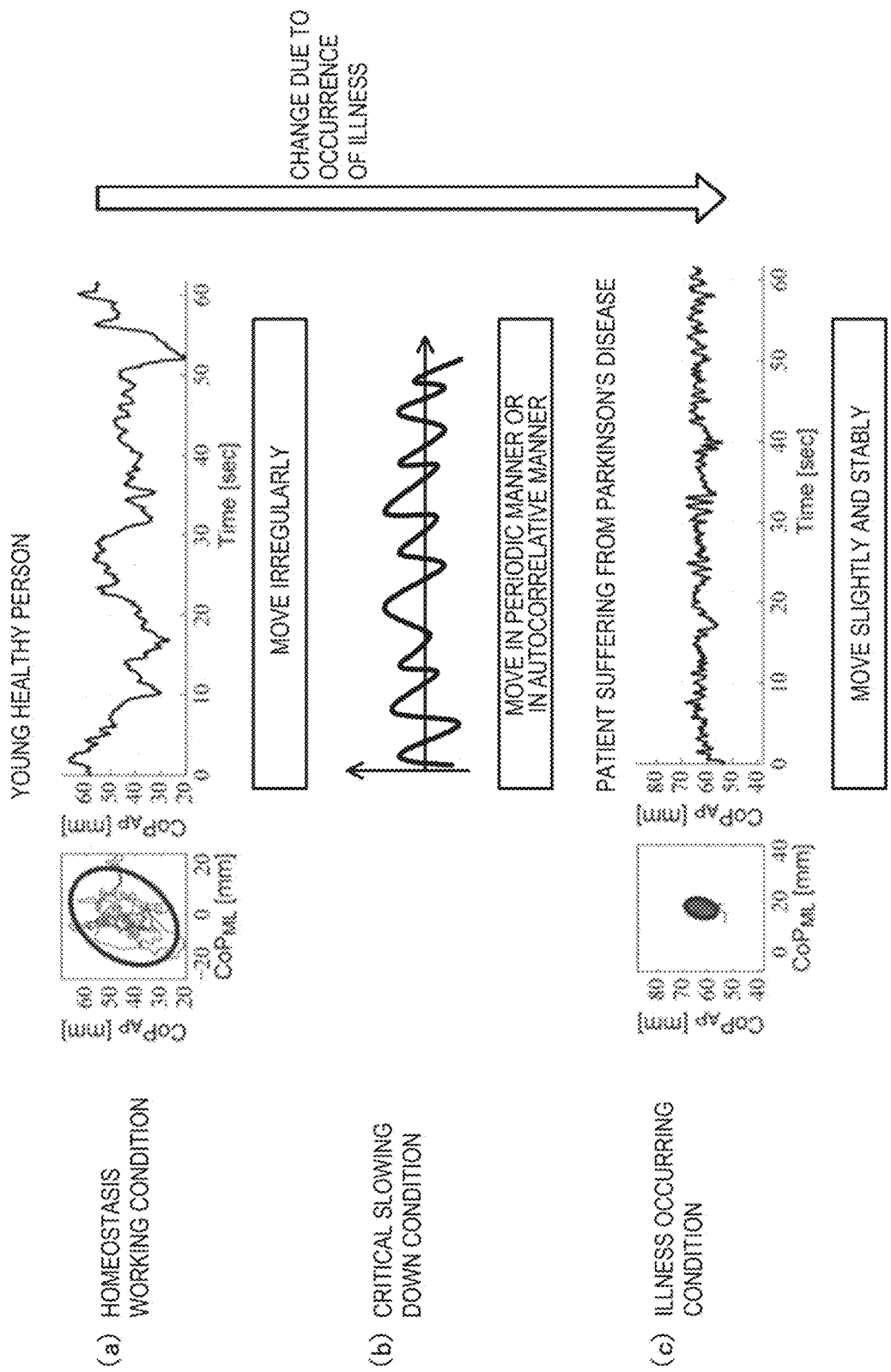
FIG. 2 shows relationships between homeostasis of movement of a head and illness.

FIG. 2 shows relationships between homeostasis of movement of a head and illness (refer to Non-Patent Documents 1 and 2). Each of the graphs in FIG. 2 shows movement of a head as viewed from above. In FIG. 2, (a) shows a normal condition in which homeostasis is maintained, (b) shows a condition between the normal condition and an illness occurring condition, which is called a "critical slowing down" condition, and (c) shows the illness occurring condition. Note that the graphs (a) and (c) in FIG. 2 are quoted from Non-Patent Document 1.

Human bodies have a function, called "homeostasis", that maintains conditions constant against disturbances. Homeostasis of movement of a head is a characteristic of maintaining the posture of the head during driving. As shown in (a) of FIG. 2, in the normal condition, the head irregularly moves due to the maintaining function of homeostasis. On the other hand, as shown in (c) of FIG. 2, when illness occurs, the head moves slightly, and the movement is stable. Meanwhile, as shown in (b) of FIG. 2, in the critical slowing down condition in which the condition is changed from the normal condition to the illness occurring condition, the head is presumed to move in a periodic manner or in an autocorrelative manner (refer to Non-Patent Document 2).

The inventors of this application focused on the above-described finding and realized that a sign of abnormality can be detected by detecting a condition change to the critical slowing down condition, from the movement of the head of a driver. More specifically, the inventors concluded that a periodic feature amount of the movement of a head can be used to detect a sign of abnormality of a driver.

The inventors of this application performed experiments as follows. A driver was made to drive a test course, and movement of the head of the driver was measured during driving. The driver was made to drive normally as usual (this corresponds to the normal condition), and then, a signal and an abnormality simulation task or complicated mental arithmetic were given to the driver (this corresponds to the abnormality sign appearing condition). A pitch angle that is an angle in a front-back direction of the head and a roll angle that is an angle in a right-left direction of the head, were measured from an image of a camera that photographs the driver, as data representing movement of the head. Thereafter, time series data of the pitch angle and the roll angle of the head were subjected to detrended fluctuation analysis (DFA), whereby autocorrelation indexes or scaling exponents a were calculated. DFA is a method for investigating scaling by removing a component that very slowly changes, i.e., a so-called "trend". The autocorrelation index or the scaling exponent a is an example of a feature amount showing periodicity of data.

Figure 3:
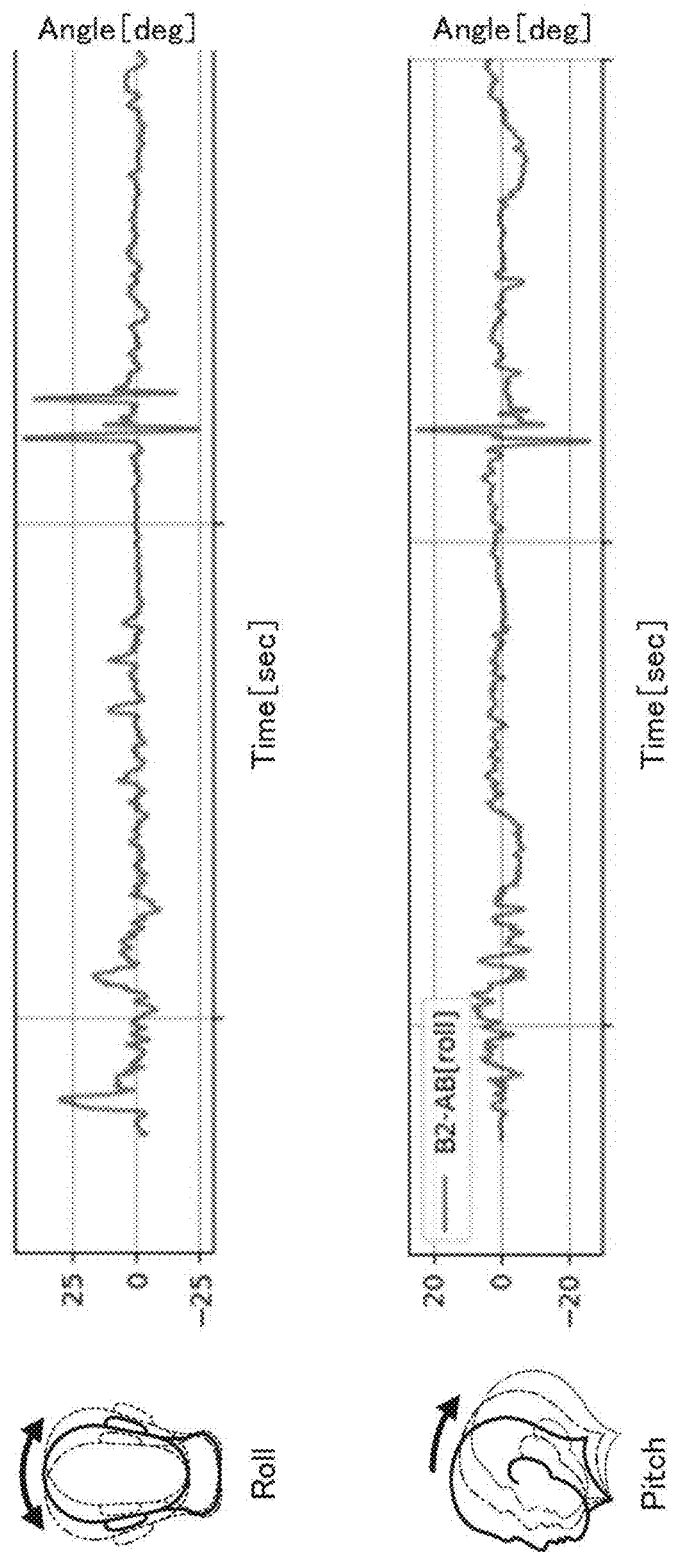
FIG. 3 shows examples of time series data of a pitch angle and a roll angle of a head.
Figure 4:
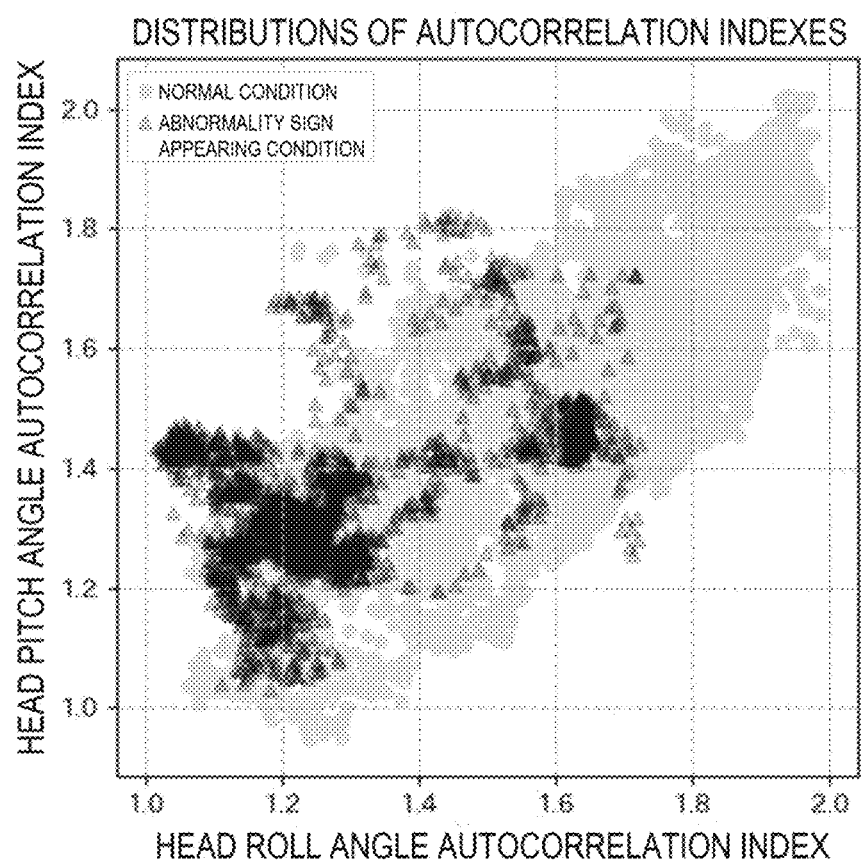
FIG. 4 is a graph showing distributions of autocorrelation indexes of the pitch angle and the roll angle of the head.

FIG. 3 shows examples of the time series data of the pitch angle and the roll angle of a head. FIG. 4 is a graph showing distributions of the autocorrelation indexes of the pitch angle and the roll angle of the head. The lateral axis represents the autocorrelation index of the roll angle, whereas the longitudinal axis represents the autocorrelation index of the pitch angle. A smaller autocorrelation index value shows stronger autocorrelation, and a greater autocorrelation index value shows weaker autocorrelation.

FIG. 4 shows that, in the abnormality sign appearing condition, the autocorrelation indexes are distributed toward the values showing stronger autocorrelation indexes, compared with those in the normal condition. These experimental results agree with the above-described finding that a head moves irregularly in the normal condition but moves periodically in the critical slowing down condition. However, as may be seen from FIG. 4 that the distribution in the normal condition spreads over a relatively large range and largely overlaps the distribution in the abnormality sign appearing condition. Thus, it is not necessarily easy to determine the abnormality sign appearing condition by using only the autocorrelation index.

Figure 5:
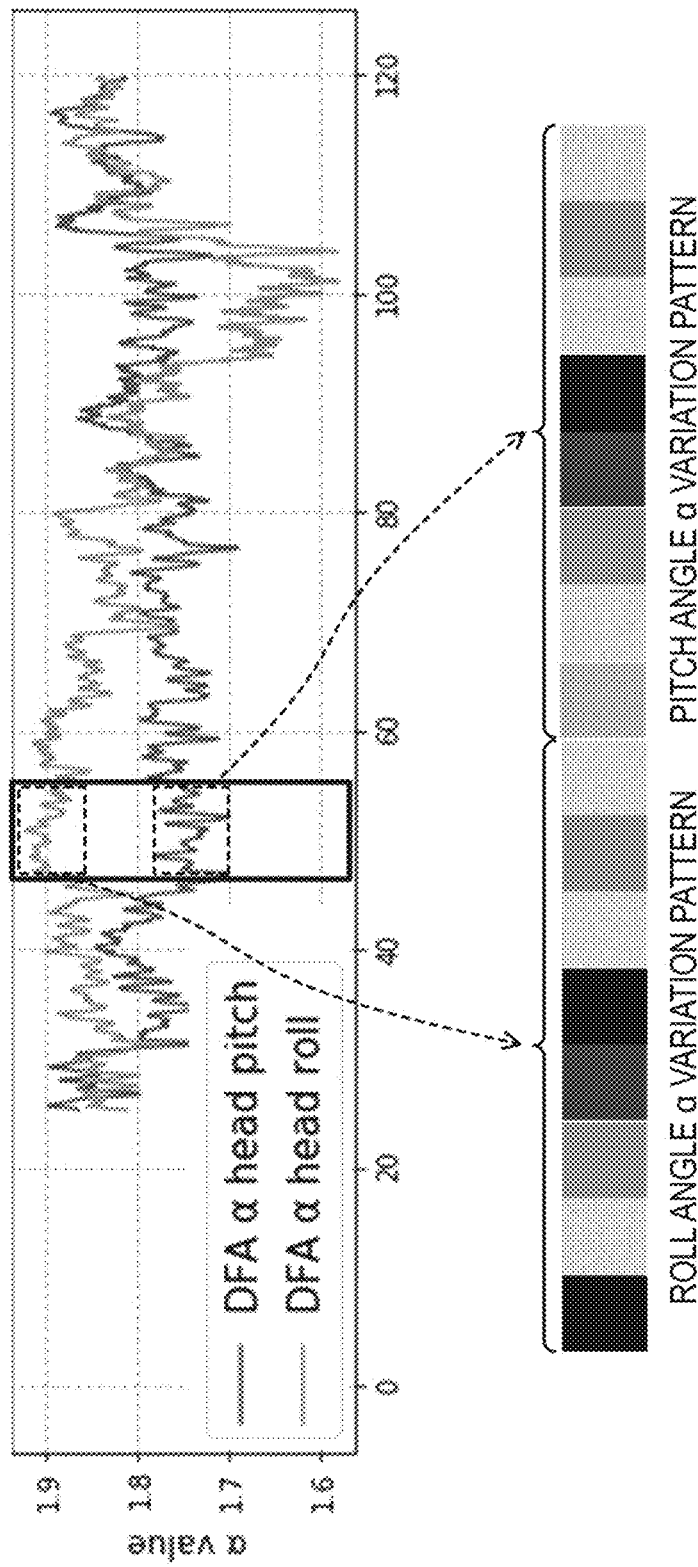
FIG. 5 is a graph showing time series variations of the autocorrelation indexes.

For this reason, the inventors of this application focused on a time series variation pattern of an autocorrelation index. As shown in FIG. 5, time series data of autocorrelation indexes were aligned in time sequence, and these data were classified into time series variation patterns. Herein, the method of the pattern classification used a nonlinear dimensionality reduction method, and more specifically, uniform manifold approximation and projection (UMAP).

Figure 6:
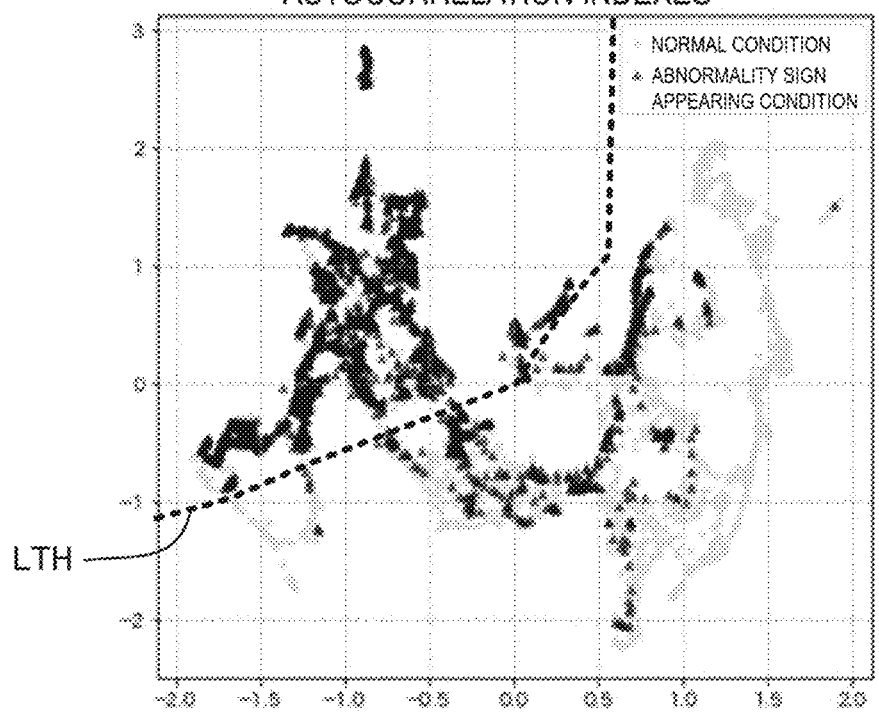
FIG. 6 is a graph showing result of classifying time series variation patterns of the autocorrelation indexes.

FIG. 6 shows result of classifying the time series variation patterns of the autocorrelation indexes. In FIG. 6, the time series variation patterns are dimensionally reduced to two dimensions by UMAP and are mapped into a two-dimensional map. In FIG. 6, the distribution in the normal condition and the distribution in the abnormality sign appearing condition are separated from each other more than in FIG. 4. The determination line, LTH, shown in FIG. 6, was obtained by using a support vector machine on the two-dimensional data. The determination line LTH may include a plurality of line segments to divide the two-dimensional map into regions in which a region above the determination line LTH is classified as normal while a region below the determination line LTH is classified as abnormal. Use of this determination line LTH achieved a wrong determination rate of 15% in determining the abnormality sign appearing condition. In particular, for this example determination line LTH, more normal conditions are incorrectly classified as abnormal conditions than abnormal conditions are classified as normal conditions. The exact determination line LTH may be adjusted according to the acceptability of these errors, e.g., may minimize incorrect classification of abnormal conditions.

Accordingly, the sign of abnormality of a driver can be detected by the following processes: calculation of a periodic feature amount from time series data showing movement of the head of the driver, calculation of a time series variation pattern from the calculated periodic feature amount, and comparison of the calculated time series variation pattern with a predetermined threshold. As may be seen in FIG. 6, this predetermined threshold is not a single value, but is a predetermined determination line LTH such that the determination of the condition depends on which side of the predetermined determination line LTH the detected conditions are on.

Moreover, the inventors of this application investigated how to further increase accuracy of determining the sign of abnormality. The result of further investigation revealed that there is a case in which movement of the head is similar to that in the abnormality sign appearing condition although a driver is in the normal condition.

Figure 7A:
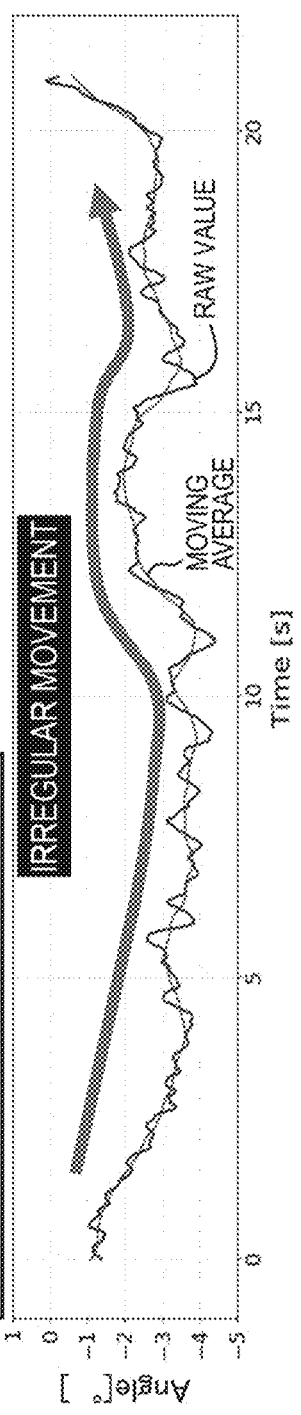
FIGS. 7A to 7C show time series data of a pitch angle of a head.
Figure 7B:
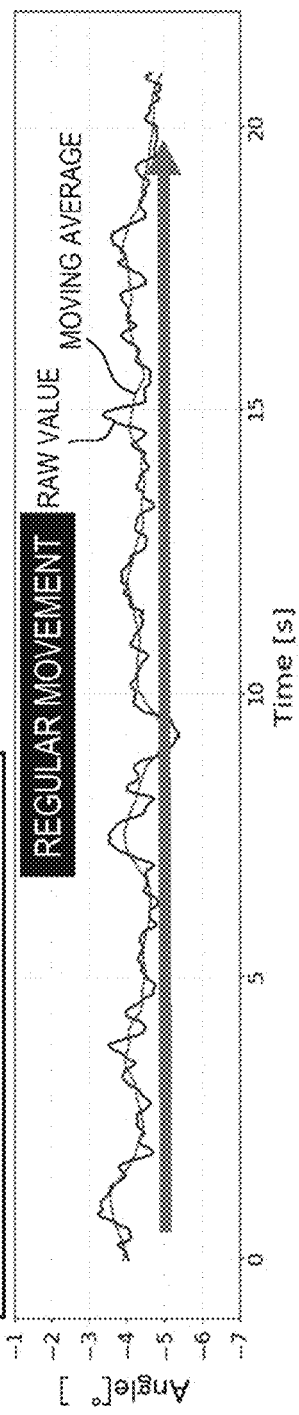
Figure 7C:
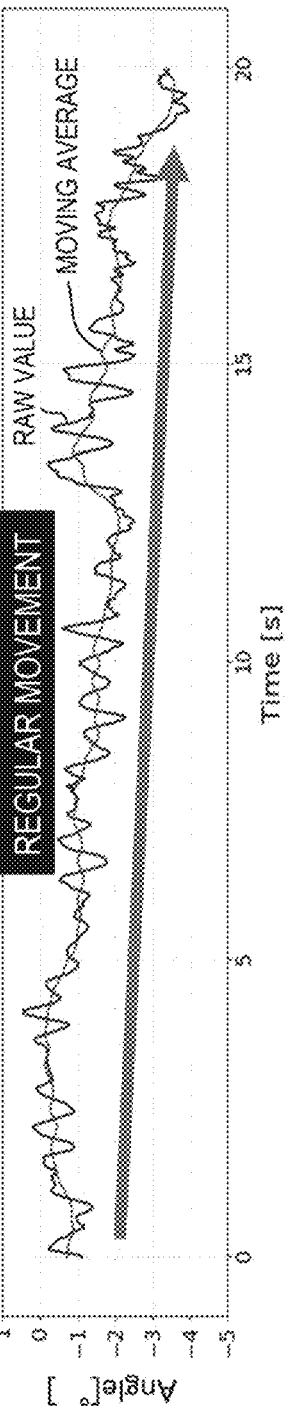

FIGS. 7A to 7C are time series data of a pitch angle of a head obtained in experiments performed by the inventors of this application. FIG. 7A shows a case in which a driver drives straight in the normal condition, FIG. 7B is a case in which the driver drives in the abnormality simulating condition, and FIG. 7C is a case in which the driver drives around corner in the normal condition. Each graph shows raw data and a moving average of the raw data. FIG. 7A shows that the head moves irregularly in the case in which the driver drives straight in the normal condition, and FIG. 7B shows that the head moves regularly in the case in which the driver drives in the abnormality simulating condition. On the other hand, FIG. 7C shows that the head moves regularly in the case in which the driver drives a corner in the normal condition.

That is, in the case in FIG. 7C, although the driver is in the normal condition, the autocorrelation index of the head pitch angle data is large, and therefore, it is difficult to distinguish from the case in FIG. 7B. It is presumed that the cause of the regular movement of the head of the driver during traveling a corner is lateral acceleration acting on the head.

Figure 8A:
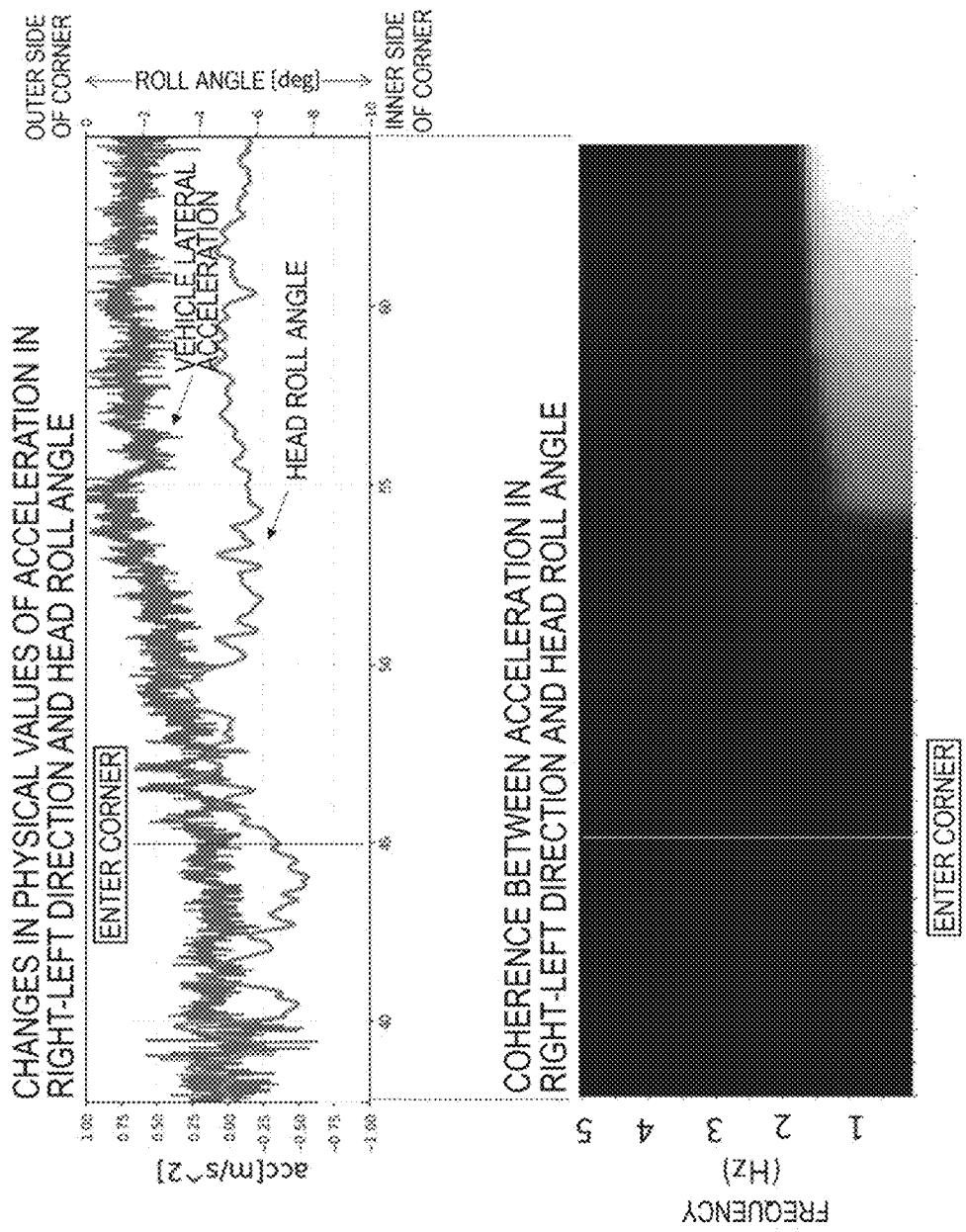

FIGS. 8A and 8B are data obtained by traveling experiments. FIG. 8A is data obtained when a vehicle enters a corner from a straight section of a circuit track, and FIG. 8B is data obtained when the condition of a driver is changed from the normal condition to the abnormality simulating condition. In FIGS. 8A and 8B, upper graphs show time series variations of vehicle lateral acceleration and a head roll angle, and lower graphs show a time series variation of coherence between the vehicle lateral acceleration and the head roll angle. In the graph of the coherence, thinner color represents higher correlation, and thicker color represents lower correlation.

The upper graph in FIG. 8A shows that the head moves in accordance with change in the lateral acceleration after the vehicle enters the corner. That is, the driver corrects the head in a direction opposite to the direction of the lateral acceleration when the head starts to be swayed by the applied lateral acceleration. Thus, correlation between the vehicle lateral acceleration and the head roll angle gradually appears after the vehicle enters the corner. On the other hand, in the case in FIG. 8B, the head roll angle is not linked with change in the vehicle lateral acceleration, and coherence is not greatly changed.

These experimental results revealed that periodicity of movement of a head tends to appear when lateral acceleration greatly acts on the head of a driver, such as going around a corner. In view of this, not performing determination in the case in which lateral acceleration greatly acts on the head of a driver is one measure to further increase accuracy of determining the sign of abnormality, because this case is anticipated to be difficult to distinguish from the abnormality sign appearing condition.

The following describes a driver condition estimating device according to this embodiment.

Figure 9:
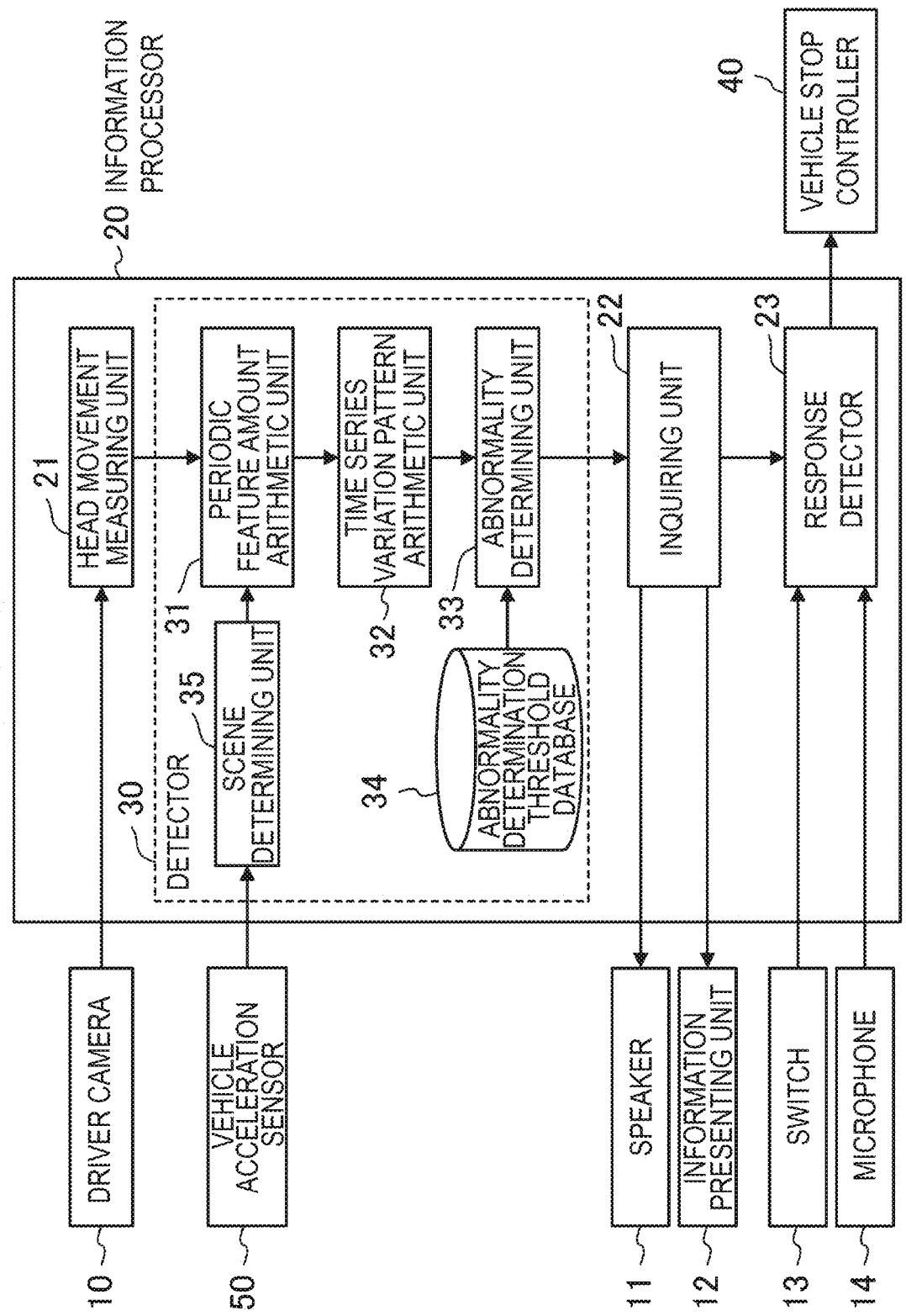
FIG. 9 is an example of a configuration of an onboard system including a driver condition estimating device according to an embodiment.

FIG. 9 is a block diagram showing an example of a configuration of an onboard system including a driver condition estimating device according to this embodiment. In the onboard system in FIG. 9, a driver camera 10, a speaker 11, an information presenting unit 12, a switch 13, and a microphone 14 are mounted in the vehicle interior. An information processor 20 is composed of, for example, a single IC chip having a processor and a memory or multiple IC chips having a processor and a memory. A vehicle stop controller 40 controls to automatically evacuate and stop the vehicle at a shoulder of a road, upon receiving an instruction from the information processor 20. A vehicle acceleration sensor 50 is provided to the vehicle.

Figure 11:
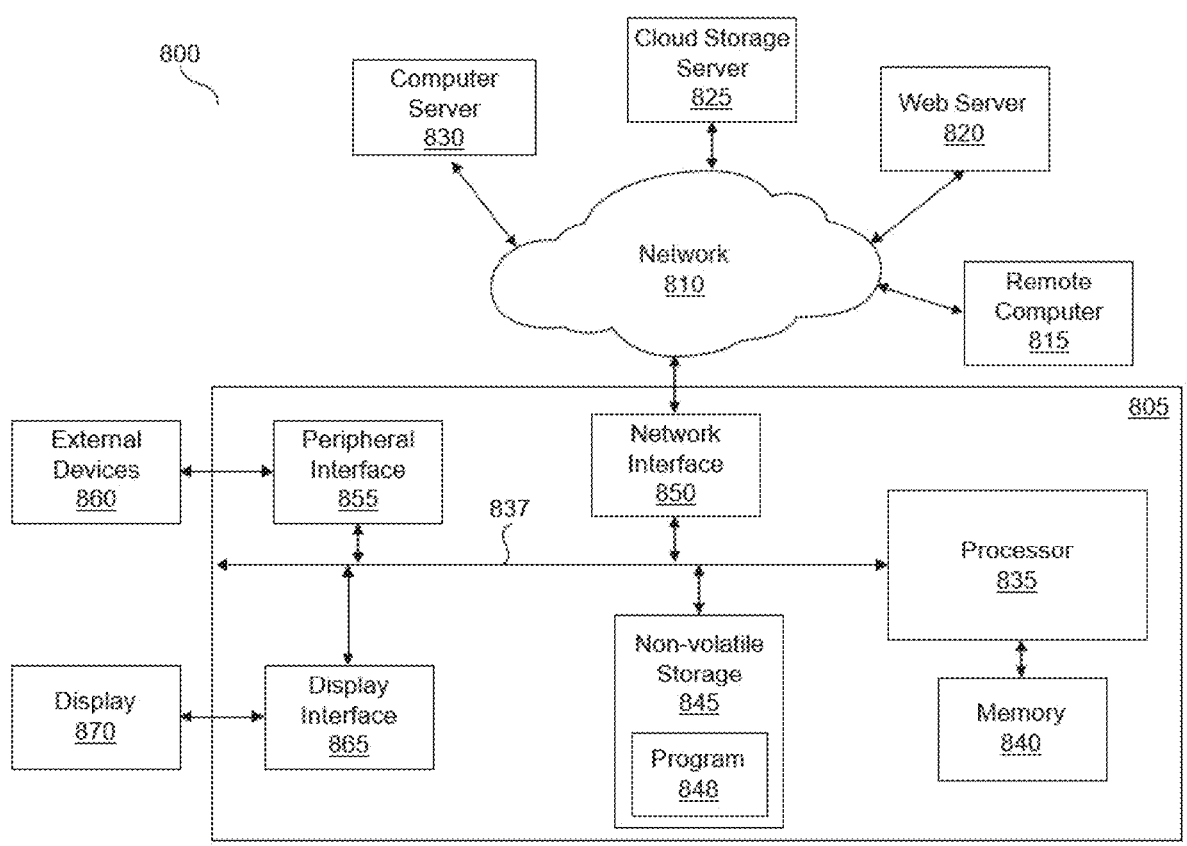
FIG. 11 is a block diagram of computer-based circuitry that may be used to implement control features of the present disclosure.

Optionally, the information processor 20 may include a processor 835 and other circuitry in system 800 of FIG. 11, which may be implemented as a single processor-based system, or a distributed processor based system, including remote processing, such as cloud based processing.

The driver camera 10 is placed, for example, at an inner side of a windshield and photographs the state of the vehicle interior, including a driver. The photographic image obtained by the driver camera 10 is transmitted to the information processor 20 by, for example, an onboard network.

In the information processor 20, a head movement measuring unit 21 measures movement of the head of the driver from the photographic image obtained by the driver camera 10. For example, the head of the driver is recognized in the image, and tilt angles of the head, e.g., a pitch angle and a roll angle, are measured. The processing in the head movement measuring unit 21 can be implemented by an existing image processing technique. The processing performed by the head movement measuring unit 21 provides time series data of movement of the head, as shown in FIG. 3. The time series data of movement of the head is transmitted to a detector 30 for detecting the sign of abnormality of a driver.

The detector 30 includes a periodic feature amount arithmetic unit 31, a time series variation pattern arithmetic unit 32, an abnormality determining unit 33, an abnormality determination threshold database 34, and a scene determining unit 35. The periodic feature amount arithmetic unit 31 calculates periodic feature amounts from the time series data of movement of the head obtained by the head movement measuring unit 21. In a specific example, autocorrelation indexes or scaling exponents a are calculated as the periodic feature amounts by detrended fluctuation analysis (DFA). The periodic feature amount arithmetic unit 31 provides time series data of the periodic feature amounts, as shown in FIG. 5.

The time series variation pattern arithmetic unit 32 aligns the time series data of the periodic feature amounts obtained by the periodic feature amount arithmetic unit 31, in time sequence. The time series variation pattern arithmetic unit 32 then calculates time series variation patterns from the aligned time series data and classifies them into patterns. In a specific example, the time series data of the periodic feature amounts are dimensionally reduced to be converted into two-dimensional data by using UMAP, which is one of nonlinear dimensionality reduction methods.

The abnormality determining unit 33 compares the data obtained by the time series variation pattern arithmetic unit 32, with a threshold stored in the abnormality determination threshold database 34, to determine whether the sign of abnormality appears in the driver. For example, the determination line LTH of the two-dimensional map in FIG. 6 corresponds to the threshold stored in the abnormality determination threshold database 34. The abnormality determining unit 33 determines whether the sign of abnormality appears in the driver, by examining on which side of the determination line LTH the data obtained by the time series variation pattern arithmetic unit 32 exists in the two-dimensional map.

The scene determining unit 35 receives output of the vehicle acceleration sensor 50 and determines whether traveling of the vehicle is in a scene where the sign of abnormality of the driver is difficult to detect, such as a scene during traveling a corner. For example, acceleration in the right-left direction of the vehicle, which is recognized from the output of the vehicle acceleration sensor 50, is used as lateral acceleration acting on the head of the driver, and whether this lateral acceleration exceeds a predetermined value is determined. In the case in which the lateral acceleration exceeds the predetermined value, the scene determining unit 35 determines that traveling is in the scene where the sign of abnormality of the driver is difficult to detect. The periodic feature amount arithmetic unit 31 does not calculate a periodic feature amount in the case in which the scene determining unit 35 determines that traveling is in the scene where the sign of abnormality of the driver is difficult to detect.

The detector 30 outputs a request for inquiry to the driver, to an inquiring unit 22 in response to the abnormality determining unit 33 determining that the sign of abnormality appears.

The inquiring unit 22 inquires the driver upon receiving the request for inquiry to the driver from the detector 30. This inquiry is made in order to confirm the intention of the driver to emergently evacuate the vehicle by automated driving. The inquiry is performed, for example, by using voice sound from the speaker 11 or by showing it via the information presenting unit 12, such as a monitor or display.

A response detector 23 detects a response of the driver to the inquiry provided by the inquiring unit 22. The driver responds, for example, by operating the switch 13 or by speaking via the microphone 14. When the intention of the driver is confirmed or when no response is received from the driver, the information processor 20 instructs the vehicle stop controller 40 to automatically evacuate and stop the vehicle at a shoulder of a road.

The driver condition estimating device according to this embodiment includes at least the head movement measuring unit 21 and the detector 30 of the information processor 20. In some cases, the driver condition estimating device according to this disclosure also includes the driver camera 10.

Figure 10:
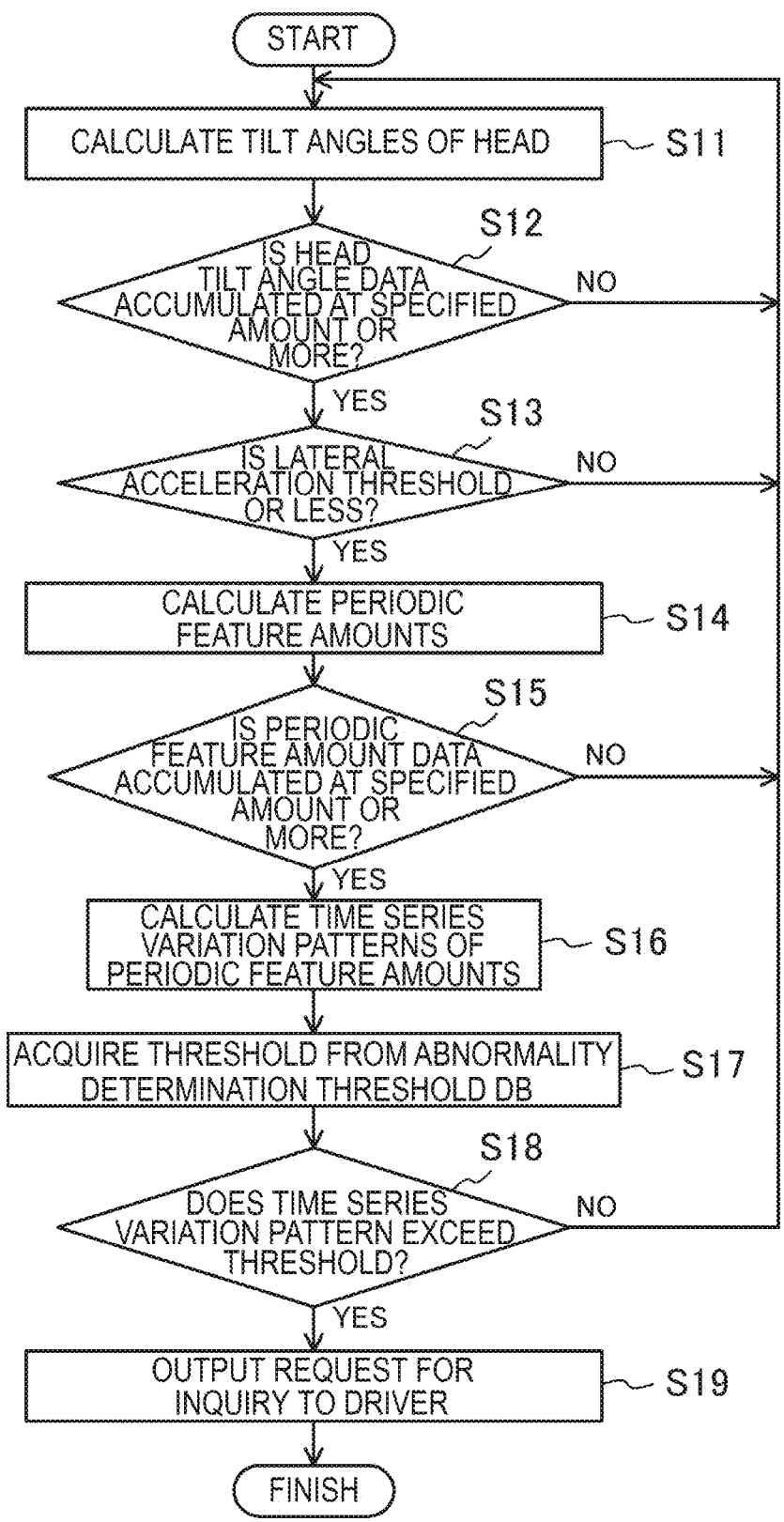
FIG. 10 is an example of a flow of processing of estimating condition of a driver in the embodiment.

FIG. 10 is a flowchart showing an example of a flow of processing of estimating condition of a driver. First, the head movement measuring unit 21 recognizes an image of the head of a driver in a photographic image obtained by the driver camera 10 and calculates tilt angles, which are a pitch angle and a roll angle herein, of the recognized head (S11). This calculation may be performed at a regular interval, e.g., 100 ms. After the tilt angle data of the head is accumulated at a specified amount or more (YES in S12), the scene determining unit 35 determines whether lateral acceleration acting on the head of the driver is a threshold or less, from output of the vehicle acceleration sensor 50 (S13). In the case in which the lateral acceleration is the threshold or less, the processing advances to step S14, and periodic feature amounts are calculated. Otherwise, in the case in which the lateral acceleration exceeds the threshold, it is determined that traveling is in the scene where the sign of abnormality of the driver is difficult to detect, and periodic feature amounts are not calculated.

In step S14, the periodic feature amount arithmetic unit 31 of the detector 30 calculates periodic feature amounts from time series data of the tilt angles of the head. In a specific example, autocorrelation indexes or scaling exponents a are calculated as the periodic feature amounts by DFA. The periodic feature amounts are calculated by changing a time range of the target tilt angle data. For example, the periodic feature amounts may be calculated using 256 pieces of tilt angle data at every 100 ms.

After the periodic feature amount data is accumulated at a specified amount or more (YES in S15), the time series variation pattern arithmetic unit 32 of the detector 30 calculates time series variation patterns from the periodic feature amount data (S16). In a specific example, the time series data of the periodic feature amounts are dimensionally reduced to be converted into two-dimensional data by using UMAP, which is one of nonlinear dimensionality reduction methods. The time series variation patterns are calculated by changing a time range of the target periodic feature amount data. For example, the time series variation patterns are calculated by using 256 pieces of periodic feature amount data at every 100 ms.

Thereafter, the abnormality determining unit 33 of the detector 30 acquires a threshold held in the abnormality determination threshold database 34 (S17). In a specific example, information of a determination line in a two-dimensional map of classified patterns, such as the determination line LTH shown in FIG. 6, is acquired as the threshold. Then, the two-dimensional data of the time series variation patterns obtained in step S16 and the determination line are compared with each other (S18). The abnormality determining unit 33 determines that the sign of abnormality appears in the case in which the two-dimensional data exists on an abnormality sign side beyond the determination line (YES in S18). At this time, the detector 30 outputs a request for inquiry to the driver, to the inquiring unit 22 (S19).

Alternatively, for example, determination of the sign of abnormality may be performed such that the sign of abnormality is determined as appearing in a case in which multiple time series variation patterns exist on the abnormality sign side beyond the determination line in a consecutive manner. In another example, the sign of abnormality may be determined as appearing in a case in which time series variation patterns exist on the abnormality sign side beyond the determination line, at an amount exceeding a predetermined ratio in a predetermined time period.

In the above-described flow, the detector 30 does not calculate the periodic feature amounts in the case of determining that traveling is in the scene where the sign of abnormality of the driver is difficult to detect. However, the processing is not limited to this. For example, the detector 30 may constantly calculate the periodic feature amounts, but may not calculate the time series variation patterns in the case of determining that traveling is in the scene where the sign of abnormality of the driver is difficult to detect. Alternatively, the detector 30 may constantly calculate the periodic feature amounts and the time series variation patterns, but may not perform determination of the sign of abnormality in the case of determining that traveling is in the scene where the sign of abnormality of the driver is difficult to detect. That is, the detector 30 is configured to avoid detection of the sign of abnormality in the scene where the sign of abnormality of the driver is difficult to detect.

Thus, in this embodiment, the head movement measuring unit 21 measures movement of the head of a driver from output of the driver camera 10 that photographs the driver. The detector 30 for detecting the sign of abnormality of a driver does not detect the sign of abnormality in the case in which lateral acceleration acting on the head of a driver exceeds a predetermined value, but determines existence of the sign of abnormality of the driver in the case in which lateral acceleration acting on the head of the driver is the predetermined value or less, by these processes: calculation of a periodic feature amount from time series data showing the movement of the head of the driver, calculation of a time series variation pattern from the periodic feature amount, and comparison of the obtained time series variation pattern with a predetermined threshold. As a result, the sign of abnormality of the driver can be detected earlier with high accuracy. In addition, it is possible to measure movement of the head of the driver from a photographic image of the driver camera 10 placed in the vehicle interior, and therefore, this technique enables early detection of a sign of illness that can cause loss of the ability to drive, by using an existing onboard sensor.

The threshold that is stored in the abnormality determination threshold database 34 can be customized in accordance with a driver. For example, the threshold is initially set to a standard value, but is modified based on accumulated time series variation patterns in the normal condition, among time series variation patterns of periodic feature amounts that are calculated and accumulated by the detector 30 during traveling of the vehicle. For example, the determination line in the two-dimensional map may be modified in accordance with distribution of time series variation patterns when a driver is in the normal condition.

In the foregoing embodiment, autocorrelation indexes or scaling exponents a are calculated as periodic feature amounts, from time series data of movement of the head, by DFA. However, the method for calculating a periodic feature amount is not limited to this. For example, fast Fourier transform (FFT) may be used, or simple autocorrelation may be calculated.

The time series data of the periodic feature amounts are dimensionally reduced to be converted into two-dimensional data by using UMAP in the foregoing embodiment, but the calculation of the time series variation patterns is not limited to this. For example, the time series data of the periodic feature amounts may be dimensionally reduced to be converted into three-dimensional data by using UMAP. In this case, for example, a two-dimensional plane that is obtained by a support vector machine is used as the threshold for determining existence of the sign of abnormality. Alternatively, the time series data of the periodic feature amounts may be dimensionally reduced by a method other than UMAP. For example, a manifold learning method other than UMAP, such as locally linear embedding (LLE) or t-distributed stochastic neighbor embedding (t-SNE), may also be used. Moreover, a general dimensionality reduction method, e.g., principal component analysis (PCA), can also be employed.

Embodiments disclosed herein are not limited to automobiles. For example, embodiments disclosed herein may be used to detect sign of abnormality of a driver of a vehicle other than an automobile, such as a train.

The technique according to this disclosure may be implemented by an embodiment other than a single information processor, in some cases. For example, the detector 30 may be implemented by an information processor separately from the head movement measuring unit 21. In another example, the function of the detector 30 may be implemented by an information processor that is not mounted on a vehicle, such as a smart phone or a tablet carried by a driver. Alternatively, one or more or all of arithmetic operations that are performed by the detector 30, may be executed by cloud computing.

The following description relates to a computer environment in which embodiments of the present disclosure may be implemented. This environment may include an embedded computer environment, local multi-processor embodiment, remote (e.g., cloud-based) environment, or a mixture of all the environments.

FIG. 11 illustrates a block diagram of a computer that may implement the various embodiments described herein. The present disclosure may be embodied as a system, a method, and/or a computer program product. The computer program product may include a computer readable storage medium on which computer readable program instructions are recorded that may cause one or more processors to carry out aspects of the embodiment.

The non-transitory computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or compute server, or any combination of these computing devices. The remote computer or compute server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 11 is a functional block diagram illustrating a networked system 800 of one or more networked computers and servers. In an embodiment, the hardware and software environment illustrated in FIG. 8 may provide an exemplary platform for implementation of the software and/or methods according to the present disclosure.

Referring to FIG. 11, a networked system 800 may include, but is not limited to, computer 805, network 810, remote computer 815, web server 820, cloud storage server 825 and computer server 830. In some embodiments, multiple instances of one or more of the functional blocks illustrated in FIG. 8 may be employed.

Additional detail of computer 805 is shown in FIG. 8. The functional blocks illustrated within computer 805 are provided only to establish exemplary functionality and are not intended to be exhaustive. And while details are not provided for remote computer 815, web server 820, cloud storage server 825 and compute server 830, these other computers and devices may include similar functionality to that shown for computer 805.

Computer 805 may be built into the automobile, a personal computer (PC), a desktop computer, laptop computer, tablet computer, netbook computer, a personal digital assistant (PDA), a smart phone, or any other programmable electronic device capable of communicating with other devices on network 810.

Computer 805 may include processor 835, bus 837, memory 840, non-volatile storage 845, network interface 850, peripheral interface 855 and display interface 865. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 835 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 837 may be a proprietary or industry standard high-speed parallel or serial peripheral interconnect bus, such as ISA, PCI, PCI Express (PCI-e), AGP, and the like.

Memory 840 and non-volatile storage 845 may be computer-readable storage media. Memory 840 may include any suitable volatile storage devices such as Dynamic Random Access Memory (DRAM) and Static Random Access Memory (SRAM). Non-volatile storage 845 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 848 may be a collection of machine readable instructions and/or data that is stored in non-volatile storage 845 and is used to create, manage and control certain software functions that are discussed in detail elsewhere in the present disclosure and illustrated in the drawings. In some embodiments, memory 840 may be considerably faster than non-volatile storage 845. In such embodiments, program 848 may be transferred from non-volatile storage 845 to memory 840 prior to execution by processor 835.

Computer 805 may be capable of communicating and interacting with other computers via network 810 through network interface 850. Network 810 may be, for example, a local area network (LAN), a wide area network (WAN) such as the Internet, or a combination of the two, and may include wired, wireless, or fiber optic connections. In general, network 810 can be any combination of connections and protocols that support communications between two or more computers and related devices.

Peripheral interface 855 may allow for input and output of data with other devices that may be connected locally with computer 805. For example, peripheral interface 855 may provide a connection to external devices 860. External devices 860 may include input devices, e.g., any or all of the devices in the information acquisition means 10 and/or other suitable input devices, and output devices, e.g., any or all of the various actuator devices AC and/or other suitable output devices, e.g., a speaker. External devices 860 may also include portable computer-readable storage media such as, for example, thumb drives, portable optical or magnetic disks, and memory cards. Software and data used to practice embodiments of the present disclosure, for example, program 848, may be stored on such portable computer-readable storage media. In such embodiments, software may be loaded onto non-volatile storage 845 or, alternatively, directly into memory 840 via peripheral interface 855. Peripheral interface 855 may use an industry standard connection, such as RS-232 or Universal Serial Bus (USB), to connect with external devices 860.

Display interface 865 may connect computer 805 to display 870, e.g., a head-up display or a screen of a car navigation system. Display 870 may be used, in some embodiments, to present a command line or graphical user interface to a user of computer 805. Display interface 865 may connect to display 870 using one or more proprietary or industry standard connections, such as VGA, DVI, DisplayPort and HDMI.

As described above, network interface 850, provides for communications with other computing and storage systems or devices external to computer 805. Software programs and data discussed herein may be downloaded from, for example, remote computer 815, web server 820, cloud storage server 825 and compute server 830 to non-volatile storage 845 through network interface 850 and network 810. Furthermore, the systems and methods described in this disclosure may be executed by one or more computers connected to computer 805 through network interface 850 and network 810. For example, in some embodiments the systems and methods described in this disclosure may be executed by remote computer 815, computer server 830, or a combination of the interconnected computers on network 810.

Data, datasets and/or databases employed in embodiments of the systems and methods described in this disclosure may be stored and or downloaded from remote computer 815, web server 820, cloud storage server 825 and compute server 830.

The embodiment is described above by way of example only and is not intended to limit the scope of this disclosure. The scope of this disclosure is defined by the claims, and modifications and alterations belonging to the scope equivalent to the scope of the claims all fall within the scope of this disclosure.

The invention claimed is:

1. A driver condition estimating device configured to estimate condition of a driver who is driving a vehicle, the driver condition estimating device comprising:
    circuitry configured to:
    measure movement of a head of the driver from output of a camera that photographs the driver; and
    detect a sign of abnormality of the driver from the movement of the head,
    on condition that lateral acceleration acting on the head of the driver exceeds a predetermined value,
    determine no detection of the sign of abnormality; and
    on condition that lateral acceleration acting on the head of the driver is the predetermined value or less,
    generate time series data from the movement of the head over time;
    calculate a periodic feature amount from the time series data;
    calculate a time series variation pattern from the calculated periodic feature amount; and
    compare the calculated time series variation pattern with a predetermined threshold to determine existence of the sign of abnormality of the driver.

2. The driver condition estimating device according to claim 1, wherein the circuitry is configured to determine whether lateral acceleration acting on the head of the driver exceeds the predetermined value, from output of a sensor for measuring a movement state of the vehicle.

3. The driver condition estimating device according to claim 2, wherein the circuitry is configured to:
    recognize a head of the driver in a photographic image obtained by the camera, and
    measure movement of the head of the driver from the photographic image, wherein
    the movement of the head of the driver includes angles of the head.

4. The driver condition estimating device according to claim 2, wherein the circuitry is configured to:
    calculate periodic feature amounts from the time series data of movement of the head, and
    calculate autocorrelation indexes as the periodic feature amounts by detrended fluctuation analysis.

5. The driver condition estimating device according to claim 2, wherein the circuitry is configured to:
    output an inquiry to the driver in response to the abnormality being determined, wherein the inquiry is at least one of a vocal inquiry output by a speaker in the vehicle and a visual inquiry shown on a display in the vehicle.

6. The driver condition estimating device according to claim 2, wherein the circuitry is configured to:
    dimensionally reduce time series data of the calculated periodic feature amount by using a nonlinear dimensionality reduction method to obtain two-dimensional data as the time series variation pattern; and
    determine existence of the sign of abnormality of the driver from the obtained two-dimensional data by using a determination line in a two-dimensional map as the predetermined threshold.

7. The driver condition estimating device according to claim 6, wherein the circuitry is configured to:
    recognize a head of the driver in a photographic image obtained by the camera, and
    measure movement of the head of the driver from the photographic image, wherein
    the movement of the head of the driver includes angles of the head.

8. The driver condition estimating device according to claim 6, wherein the circuitry is configured to:
    calculate periodic feature amounts from the time series data of movement of the head, and
    calculate autocorrelation indexes as the periodic feature amounts by detrended fluctuation analysis.

9. The driver condition estimating device according to claim 6, wherein the circuitry is configured to:
    output an inquiry to the driver in response to the abnormality being determined, wherein the inquiry is at least one of a vocal inquiry output by a speaker in the vehicle and a visual inquiry shown on a display in the vehicle.

10. The driver condition estimating device according to claim 1, wherein the circuitry is configured to:
    dimensionally reduce time series data of the calculated periodic feature amount by using a nonlinear dimensionality reduction method to obtain two-dimensional data as the time series variation pattern; and
    determine existence of the sign of abnormality of the driver from the obtained two-dimensional data by using a determination line in a two-dimensional map as the predetermined threshold.

11. The driver condition estimating device according to claim 1, wherein the circuitry is configured to:
    recognize a head of the driver in a photographic image obtained by the camera, and
    measure movement of the head of the driver from the photographic image, wherein
    the movement of the head of the driver includes angles of the head.

12. The driver condition estimating device according to claim 11, wherein the circuitry is configured to:
    calculate periodic feature amounts from the time series data of movement of the head, and
    calculate autocorrelation indexes as the periodic feature amounts by detrended fluctuation analysis.

13. The driver condition estimating device according to claim 12, wherein the circuitry is configured to:
    output an inquiry to the driver in response to the abnormality being determined, wherein the inquiry is at least one of a vocal inquiry output by a speaker in the vehicle and a visual inquiry shown on a display in the vehicle.

14. The driver condition estimating device according to claim 11, wherein the circuitry is configured to:
    output an inquiry to the driver in response to the abnormality being determined, wherein the inquiry is at least one of a vocal inquiry output by a speaker in the vehicle and a visual inquiry shown on a display in the vehicle.

15. The driver condition estimating device according to claim 1, wherein the circuitry is configured to:
calculate periodic feature amounts from the time series data of movement of the head, and
calculate autocorrelation indexes as the periodic feature amounts by detrended fluctuation analysis.

16. The driver condition estimating device according to claim 1, wherein the circuitry is configured to:
output an inquiry to the driver in response to the abnormality being determined, wherein the inquiry is at least one of a vocal inquiry output by a speaker in the vehicle and a visual inquiry shown on a display in the vehicle.

17. A driver condition estimating method for estimating condition of a driver who is driving a vehicle, the driver condition estimating method comprising:
on condition that lateral acceleration acting on a head of the driver exceeds a predetermined value,
performing no detection of a sign of abnormality; and
on condition that lateral acceleration acting on the head of the driver is the predetermined value or less,
generating time series data from movement of the head over time;
calculating a periodic feature amount from time series data;
calculating a time series variation pattern from the calculated periodic feature amount; and
comparing the calculated time series variation pattern with a predetermined threshold to determine existence of the sign of abnormality of the driver.

18. A non-transitory computer readable storage including computer readable instructions that when executed by a controller cause the controller to execute a driver state determination method for a driver in a vehicle, the method comprising:
on condition that lateral acceleration acting on a head of the driver exceeds a predetermined value,
performing no detection of a sign of abnormality; and
on condition that lateral acceleration acting on the head of the driver is the predetermined value or less,
generating time series data from movement of the head over time;
calculating a periodic feature amount from the time series data;
calculating a time series variation pattern from the calculated periodic feature amount; and
comparing the calculated time series variation pattern with a predetermined threshold to determine existence of the sign of abnormality of the driver.

* * * * *